United States Patent [19]

Brazdil et al.

[11] Patent Number: 5,214,016

[45] Date of Patent: May 25, 1993

[54] METHOD OF MAKING CATALYSTS CONTAINING VANADIUM, ANTIMONY AND TIN

[75] Inventors: James F. Brazdil, Lyndhurst, Ohio; Ian R. Little, Hampton Hill, England; Joseph B. Hazen, Garfield Heights, Ohio

[73] Assignee: The Standard Oil Company, Cleveland, Ohio

[21] Appl. No.: 862,163

[22] Filed: Apr. 2, 1992

[51] Int. Cl.$^5$ .................. B01J 23/14; B01J 23/16
[52] U.S. Cl. ................... 502/202; 502/215; 502/304; 502/310; 502/338; 502/350; 502/352; 558/325
[58] Field of Search ............ 502/202, 215, 310, 502/338, 350, 352; 558/325

[56] References Cited

U.S. PATENT DOCUMENTS 3,326,819  6/1967  Newman ............... 502/350 X
4,801,568  1/1989  Brazdil et al. ........... 502/352 X

*Primary Examiner*—W. J. Shine
*Attorney, Agent, or Firm*—C. S. Lynch; M. F. Esposito; L. W. Evans

[57] ABSTRACT

Disclosed is a method of making a catalyst containing vanadium antimony and tin in the oxide state which comprises making an aqueous slurry of a mixture of source batch materials comprising compounds of the elements to be included in the final catalyst followed by drying and heat calcining the mixture to an active catalyst, using as the source batch material for tin a stannous salt of a $C_1$ to $C_{18}$ acyclic, monocarboxylic acid containing no ethylenic or acetylenic carbon-to-carbon unsaturation.

6 Claims, No Drawings

METHOD OF MAKING CATALYSTS CONTAINING VANADIUM, ANTIMONY AND TIN

This invention relates to a method for the preparation of tin-containing vanadium-antimony oxide catalysts useful for the catalytic ammoxidation of paraffins, more specifically for the preparation of catalysts for the ammoxidation of propane or isobutane to an $\alpha,\beta$-unsaturated mononitrile, acrylonitrile or methacrylonitrile.

More specifically, the invention relates to the use of a tin salt of certain organic carboxylic acids as the reagent for tin in the preparation of catalysts containing vanadium and antimony and tin in oxide form. Such catalysts are disclosed for instance in U.S. Pat. Nos. 3,681,421; 4,788,317 and 5,008,427 and one such catalyst is disclosed in British specifications 1,336,135 and 1,336,136, published in November 1973.

Not all sources of tin are equally effective as promoters in vanadium-antimony oxide catalysts for the oxidation and ammoxidation of saturated $C_3$ and $C_4$ alkanes, particularly ammoxidation. It is believed that the tin should be present in very finely divided form in the precursors of such catalysts in order for the tin to be fully reactive when the solid state reaction takes place upon calcination of the catalyst precursor mixture. Before the present invention, it was found that a tin oxide sol was a suitable source in making such catalysts; see U.S. Pat. No. 5,008,427. But ground tin oxide or tin oxide made by reacting tin metal with nitric acid are decidedly less effective sources. While a tin oxide sol is effective, it is a very expensive source.

It is an object of the present invention to provide a method of making a superior oxidation (particularly ammoxidation) catalyst while avoiding the use of tin oxide sols.

It is another object of the invention to make such a catalyst at a fraction of the expense with respect to the tin component as compared to using a tin oxide sol as the source of tin in the catalyst precursor.

Other objects, as well as aspects, features and advantages, of the invention will become apparent from a study of the specification including the specific examples.

The foregoing and other objects are accomplished by the present invention according to which there is provided a method of making a catalyst containing vanadium, antimony and tin in the oxide state which comprises making an aqueous slurry of a mixture of source batch materials comprising compounds of the elements to be included in the final catalyst, followed by drying and heat calcining the mixture to an active catalyst, using as the source batch material for a tin a stannous salt of a $C_1$ to $C_{18}$ acyclic, monocarboxylic acid containing no ethylenic or acetylenic carbon-to-carbon unsaturation. Usually, for practical reasons, this salt is a stannous salt of an acyclic monocarboxylic acid having 1 to 8 carbon atoms, more usually 1 to 4 carbon atoms, and also most often having only three elements: C, H and O, only 2 atoms of O being present per molecule of acid. Such tin (II) salts most often used in the preparation method of the invention are salts of acyclic monocarboxylic acids of the emperical formula:

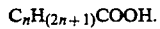

$C_nH_{(2n+1)}COOH$.

The catalyst can be made from any suitable organic or inorganic precursor compounds of V and Sb, and compounds used to introduce other optional elements into the final catalyst after calcination, as is well known in the art, such as the salts, oxides, hydroxides or metallo-organic compounds of such elements, with the tin being introduced to the batch of raw materials for preparing such catalysts in the form of the tin (II) salts of the carboxylic acids previously disclosed herein. The batch mixture of precursor materials is heated and calcined in a known manner until the final catalyst results. Examples of such raw source batch materials are of course shown in the specific working examples herein.

In making the catalysts the upper calcining temperature is usually at least 500° C., but for ammoxidation of paraffins this temperature is preferably over 750° C., most often at least 780° C.

A now preferred method of the invention is to make catalysts of the composition of the catalysts of U.S. Pat. No. 5,008,427 but by the method of the present invention.

Thus, according to this aspect of the invention there is provided a method of making a catalyst having the elements and the proportions indicated by the empirical formula:

$$VSb_mA_aD_dO_x$$

where
- A is one or more Ti, Sn, Fe, Cr, Ga, Sn always being present
- D is one or more Li, Mg, Ca, Sr, Ba, Co, Ni, Zn, Ge, Nb, Zr, Mo, W, Cu, Te, Ta, Se, Bi, Ce, In, As, B Mn and
- m is 0.8–4
- a is 0.01–2
- d is 0–2
- x is determined by the oxidation state of the cations present, which comprises making an aqueous slurry of a mixture of source batch materials comprising compounds of said elements to be included in the final catalyst, followed by drying and heat calcining the mixture to an active catalyst, using as the source batch material for tin a stannous salt of a $C_1$ to $C_{18}$ acyclic, monocarboxylic acid containing no ethylenic or acetylenic carbon-to-carbon unsaturation, drying said slurry and heat calcining the mixture to an upper calcination temperature of at least 780° C. As noted in said U.S. patent this upper calcination temperature can be up to 1200° C., but is most often not over 1050° C.

In another aspect of the present invention, there is provided a process for making an $\alpha,\beta$-unsaturated mononitrile selected from acrylonitrile and methacrylonitrile, by the catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to $NH_3$ in the range from 2.5 to 16 and a mole ratio of said paraffin to $O_2$ in the range from 1 to 10, said catalyst having the emperical composition recited in the last previous paragraph, said catalyst having been made by the method of the last previous paragraph.

The following examples of making the catalysts and the ammoxidation reactions using the catalysts so made are exemplary only and should not be understood to be in any way limiting.

The stannous acetate used in some of the examples to follow was made as follows:

25 g of SnO were refluxed under nitrogen with 125 ml of glacial acetic acid and 75 ml of water for about eight hours. The mixture was then cooled under nitrogen to room temperature and filtered to remove any unreacted SnO. The filtrate was then slowly evaporated using a roto-vap to yield white solid tin(II) acetate which was stored in a desiccator with sodium hydroxide to remove any residual acetic acid.

Also, other tin(II) esters used in other examples were made as follows:

Preparation of Tin(II)Formate:

25 g of SnO were refluxed under nitrogen with 625 ml of 60 wt % formic acid solution for 1.5 hours. The hot mixture was then filtered to remove any unreacted SnO and then cooled and stored in a stoppered flask.

Preparation of Tin(II) Propionate:

25 g of SnO were refluxed under nitrogen with 100 g propionic acid for 2.5 hours. The hot mixture was then filtered to remove any unreacted SnO and then cooled and stored in a stoppered flask.

Preparation of Tin(II) Butyrate:

25g of SnO were refluxed under nitrogen with 100 butyric acid and 75 g of water. The hot mixture was then filtered to remove any unreacted SnO and then cooled and stored in a stoppered flask.

EXAMPLE 1

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry. 12.287 g of tin(II) acetate, dissolved in enough glacial acetic acid to effect complete dissolution, were then added to the slurry. The resulting mixture was then allowed to evaporate to near dryness on the hot plate with constant stirring. The resulting black paste was further dried in an oven at 120° C. overnight. A portion of the dried material was placed in a quartz tube and a constant flow of air was passed through the tube and over the material. The tube was positioned in a vertical tube furnace and the furnace temperature was increased from room temperature to 650° C. at a rate of about 2°/minute. The temperature was then held at 650° C. for eight hours. The catalyst was then cooled to room temperature and the heat treated material was crushed and sieved and the 20-35 mesh particles were collected. A portion of these particles was then heat treated in air in a furnace for three hours at 810° C. This material was then washed four times with isobutanol by placing the material in a course glass frit funnel and allowing fresh isobutanol to pass over the particles and through the frit. The amount of isobutanol used in each washing was about 6.25 ml per gram of catalyst washed. After the final washing, the catalyst particles were placed in an oven at 120° C. for several hours to remove the residual isobutanol from the particles.

EXAMPLE 2

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss. Fresh water was added periodically to replace water than boiled off. The mixture was boiled for about three hours to produce a gray-black slurry. 12.287 g of tin(II) acetate, dissolved in enough glacial acetic acid to effect complete dissolution, were then added to the slurry. The resulting mixture was then allowed to evaporate to near dryness on the hot plate with constant stirring. The resulting black paste was further dried in an oven at 120° C. overnight. The dried material was heat treated in air in a furnace for eight hours at 650° C. The heat treated material was crushed and sieved and the 20-35 mesh particles were collected. A portion of these particles was then heat treated in air in a furnace for three hours at 810° C. The particles were then washed with methanol for about 1.5 hours using a Soxhlet extractor. After washing, the catalyst particles were placed in an oven at 120° C. for several hours to remove the residual methanol from the particles.

EXAMPLE 3

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry. 12.287 g of tin(II) acetate, dissolved in enough glacial acetic acid to effect complete dissolution, were then added to the slurry. The resulting mixture was then allowed to evaporate to near dryness on the hot place with constant stirring. The resulting black paste was further dried in an oven at 120° C. overnight. The dried material was heat treated in air in a furnace for eight hours at 650° C. The heat treated material was crushed and sieved and the 20-35 mesh particles were collected.

A portion of these particles was then heat treated in air in a furnace to three hours at 810° C. This material was then washed three times with isobutanol by placing the material in a course glass frit funnel and allowing fresh isobutanol to pass over the particles and through the frit. The amount of isobutanol used in each washing was about 6.25 ml per gram of catalyst washed. After the final washing, the catalyst particles were placed in an oven at 120° C. for several hours to remove the residual isobutanol from the particles.

EXAMPLE 4

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot place with constant stirring. A watch glass was placed over the top of the beaker to reduce the amount of water loss. Fresh water was added periodically to replace water that boiled off. The mixture was boiled for about three hours to produce a gray-black slurry. 12.287 g of tin(II) acetate, dissolved in enough glacial acetic acid to effect complete dissolution, were then added to the slurry. The resulting mixture was then allowed to evaporate to near dryness on the hot plate with constant stirring. The resulting black paste was further dried in an oven at 120° C. overnight. A portion of the dried material was heat treated in air in a furnace for three hours at 290° C., three hours at 425° C., and eight hours at 650° C., temperature and crushed and sieved, and the 20–35 mesh particles then heat treated in air in a furnace for three hours at 810° C.

This material was then washed three times with isobutanol by placing the material in a course glass frit funnel and allowing fresh isobutanol to pass over the particles and through the frit. The amount of isobutanol used in each washing was about 6.25 ml per gram of catalyst washed. After the final washing, the catalyst particles were placed in an oven at 120° C. for several hours to remove the residual isobutanol from the particles.

EXAMPLE 5 (COMPARATIVE)

26.91 g of $V_2O_5$ were added to a solution of 900 ml water and 100 ml of 30% $H_2O_2$ solution. After bubbling of the mixture stopped, 64.36 g of $Sb_2O_3$ were added along with 8.87 g of $SnO_2$ powder. The mixture was heated to boiling on a hot plate with constant stirring. A watch glass was placed over the top of the beaker to reduce the amount of water loss. Fresh water was added periodically to replace water that boiled off. The mixture was boiled for about 2.5 hours to produce a gray-black slurry. The resulting mixture was then allowed to evaporate to near dryness on the hot plate with constant stirring. The resulting black paste was further dried in an oven at 120° C. overnight. The dried material was heat treated in air in a furnace for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. After washing, the catalyst particles were placed in an oven at 120° C. for several hours to remove the residual isobutanol from the particles.

EXAMPLE 6 (COMPARATIVE)

6.86 g of tin metal powder were slurried in 200 ml water, 20 ml of concentrated nitric acid solution and 100 ml 30% $H_2O_2$ were added. The mixture was heated to about 80° C. for three hours to produce a white slurry of tin oxide. In a separate beaker 26.38 g of $V_2O_5$ were added to a solution of 900 ml of water and 140 ml of 30% $H_2O_2$ and 28 g concentrated nitric acid solution. After bubbling of the mixture stopped, the previously prepared tin oxide slurry was added along with 63.19 g of $Sb_2O_3$. The resulting mixture was then heated with constant stirring on a hot plate and allowed to evaporate to near dryness. The paste was further dried in an oven at 120° C. overnight. The dried material was heat treated in air in a furnace for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. After washing, the catalyst particles were placed in an oven at 120° C. for several hours to remove the residual isobutanol from the particles.

EXAMPLE 7

26.91 of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry. 217.8 g of the previously prepared tin(II) formate solution were then added to the slurry. The resulting mixture was then allowed to evaporate to near dryness on the hot plate with constant stirring. The resulting black paste was further dried in an oven at 120° C. overnight. A portion of the dried material was heat treated in air in a furnace for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. The catalyst was washed twice in this manner. After washing, the catalyst particles were placed in an oven at 120° C. for several hours to remove the residual isobutanol from the particles.

EXAMPLE 8

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry. 51.5 g of the previously prepared tin(II) propionate solution were then added to the slurry. The resulting mixture was then allowed to evaporate to near dryness on the hot plate with constant stirring. The resulting black paste was further dried in an oven at 120° C. overnight. A portion of the dried material was heat treated in air in a furnace for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. The catalyst was washed twice in this manner. After washing, the catalyst particles were placed in an oven at 120° C. for several hours to remove the residual isobutanol from the particles.

EXAMPLE 9

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss.

Fresh water was added periodically to replace water that boiled off. The mixture was boiled for about three hours to produce a gray-black slurry. 51.5 g of the previously prepared tin(II) propionate solution were then added to the slurry. The resulting mixture was then allowed to evaporate to near dryness on the hot plate with constant stirring. The resulting black paste was further dried in an over at 120° C. overnight. A portion of the dried material was heat treated in air in a furnace at 290° C. for three hours, then at 425° C. for three hours, and finally for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. The catalyst was washed twice in this manner. After washing, the catalyst particles were placed in an oven at 120° C. for several hours to remove the residual isobutanol from the particles.

EXAMPLE 10

26.91 g of $V_2O_5$ were added to a solution of 900 ml water and 100 ml of 30% $H_2O_2$ solution. After bubbling of the mixture stopped, 64.36 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry. The entire previously prepared tin(II) butyrate solution was then added to the slurry. The resulting mixture was then allowed to evaporate to near dryness on the hot plate with constant stirring. The resulting black paste was further dried in an oven at 120° C. overnight. A portion of the dried material was heat treated in air in a furnace at 290° C. for three hours, then at 425° C. for three hours, and finally for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. The catalyst was washed twice in this manner. After washing, the catalyst particles were placed in an oven at 120° C. for several hours to remove the residual isobutanol from the particles.

EXAMPLE 11

27.42 g of $V_2O_5$ were added to a solution of 900 ml water and 100 ml of 30% $H_2O_2$ solution. After bubbling of the mixture stopped, 65.59 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry, 25.59 g of tin(II) ethylhexanoate were then added to the slurry. The resulting mixture was then allowed to evaporate to near dryness on the hot plate with constant stirring. The resulting black paste was further dried in an oven at 120° C. overnight. A portion of the dried material was heat treated in air in a furnace for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. The catalyst was washed three times in this manner. After washing, the catalyst particles were placed in an oven at 120° C. for several hours to remove the residual isobutanol from the particles.

EXAMPLE 12

27.42 g of $V_2O_5$ were added to a solution of 900 ml and 100 ml of 30% $H_2O_2$ solution. After bubbling of the mixture stopped, 65.59 g of $Sb_2O_3$ were added and the mixture was heated to boiling on a hot plate with constant stirring. A watch glass was placed over the top of the beaker to reduce the amount of water loss. Fresh water was added periodically to replace water that boiled off. The mixture was boiled for about three hours to produce a gray-black slurry. 25.59 g of tin(II) ethylhexanoate was then added to the slurry. The resulting mixture was then allowed to evaporate to near dryness on the hot plate with constant stirring. The resulting black paste was further dried in an oven at 120° C. overnight. A portion of the dried material was heat treated in air in a furnace at 290° C. for three hours, then at 425° C. for three hours, and finally for eight hours at 650° C. The heat treated material was crushed and sieved and the 20–35 mesh particles were collected. A portion of these particles was then heat treated in air in a furnace for three hours at 810° C. This material was then washed with isobutanol by placing the material in a course glass frit funnel and allowing fresh isobutanol to pass over the particles and through the frit. The amount of isobutanol used was about 6.25 ml per gram of catalyst washed. The catalyst was washed three times in this manner. After washing, the catalyst particles were placed in an oven at 120° C. for several hours to remove the residual isobutanol from the particles.

In the following ammoxidation examples summarized in Table 1, the catalyst is in a tubular ⅜ inch I.D. titanium metal fixed bed reactor. The reactor is equipped with a preheat leg and is immersed in a temperature controlled molten salt bath. The feed is fed to the catalyst for one hour before collection of product, unless otherwise noted; the runs of each example last 30–60 minutes during which the product is collected for analysis.

TABLE 1

| Example[5] No. | Catalyst Example[5] No. | Mole Ratios $C_3/NH_3/O_2/H_2O$[6] | Temp. °C. | CT Secs[4] | Percent Propane Conversion | Propane: Mole % Conversion to AN[2] | HCN | $C_3=$[3] | % Selectivity[1] AN | AN + HCN |
|---|---|---|---|---|---|---|---|---|---|---|
| 13 | 1 | 5/1/2.8/1 | 460 | 1.2 | 15.9 | 9.4 | 1.6 | 0.6 | 58.8 | 69.2 |
| 14 | 2 | " | " | 1.1 | 15.0 | 9.1 | 1.4 | 0.3 | 60.7 | 70.0 |

TABLE 1-continued

| Example[5] No. | Catalyst Example[5] No. | Mole Ratios $C_3/NH_3/O_2/H_2O$[6] | Temp. °C. | CT Secs[4] | Percent Propane Conversion | Propane: Mole % Conversion to | | | % Selectivity[1] | |
|---|---|---|---|---|---|---|---|---|---|---|
| | | | | | | AN[2] | HCN | $C_3$=[3] | AN | AN + HCN |
| 15 | 3 | " | " | 1.4 | 18.4 | 10.2 | 1.6 | 0.4 | 55.5 | 64.1 |
| 16 | 4 | " | " | 1.6 | 17.2 | 9.9 | 1.5 | 0.4 | 57.3 | 66.3 |
| 17C | 5C | 5/0.85/2/1 | " | 0.9 | 16.3 | 6.4 | 2.1 | 1.7 | 38.9 | 52.1 |
| 18C | 6C | 5/1/2.8/1 | " | 1.3 | 18.6 | 6.1 | 2.2 | 2.1 | 33.0 | 44.6 |
| 19 | 7 | " | " | 1.0 | 16.9 | 9.1 | 1.5 | 0.6 | 53.6 | 62.2 |
| 20 | 9 | " | " | 1.6 | 15.6 | 8.7 | 1.2 | 0.5 | 56.1 | 64.1 |
| 21 | 11 | " | " | 0.9 | 16.4 | 8.9 | 1.4 | 0.2 | 54.3 | 62.8 |
| 22 | 8 | " | " | 0.6 | 17.4 | 8.9 | 1.5 | 0.7 | 51.0 | 59.7 |
| 23 | 10 | " | " | 0.6 | 15.2 | 8.2 | 1.2 | 0.4 | 53.8 | 61.9 |
| 24 | 12 | " | " | 0.9 | 15.4 | 8.6 | 1.5 | 0.3 | 55.9 | 65.6 |

[1] Selectivity based on propane
[2] AN is Acrylonitrile
[3] $C_3$= is Propylene
[4] Contact time, seconds
[5] C = Comparative example
[6] $C_3$ is Propane As will be evident to those skilled in the art, various modifications of this invention can be made or followed in the light of the foregoing disclosure and discussion without department from the spirit and scope of the disclosure or from the scope of the claims.

We claim:

1. A method of making a catalyst containing vanadium, antimony and tin in the oxide state which comprises making an aqueous slurry of a mixture of source batch materials comprising compounds of the elements to be included in the final catalyst followed by drying and heat calcining the mixture to an active catalyst, using as the source batch material for tin a stannous salt of a $C_1$ to $C_{18}$ acyclic monocarboxylic acid containing no ethylenic or acetylenic carbon-to-carbon unsaturation.

2. A method of claim 1 wherein said source batch material for tin is a stannous salt of a $C_1$ to $C_8$ acyclic monocarboxylic acid containing no ethylenic or acetylenic carbon-to-carbon unsaturation.

3. A method of claim 1 wherein said source batch material for tin is a stannous salt of a $C_1$ to $C_4$ acyclic monocarboxylic acid containing no ethylenic or acetylenic carbon-to-carbon unsaturation.

4. A method of making a catalyst having the elements and the proportions indicated by the empirical formula:

$$VSb_m A_a D_d O_x$$

where

A is one or more Ti, Sn, Fe, Cr, Ga, Sn always being present,

D is one or more Li, Mg, Ca, Sr, Ba, Co, Ni, Zn, Ge, Nb, Zr, Mo, W, Cu, Te, Ta, Se, Bi, Ce, In, As, B, Mn and m is 0.8–4 a is 0.01–2 d is 0–2 x is determined by the oxidation state of the cations present, which comprises making an aqueous slurry of a mixture of source batch materials comprising compounds of said elements to be included in the final catalyst, using as the source batch material for tin a stannous salt of a $C_1$ to $C_{18}$ acyclic monocarboxylic acid maintaining no ethylenic or acetylenic carbon-to-carbon unsaturation, drying said slurry and heat calcining the mixture to an upper calcination temperature of at least 780° C.

5. A method of claim 4 wherein said source batch material for tin is a stannous salt of a $C_1$ to $C_8$ acyclic monocarboxylic acid containing no ethylenic or acetylenic carbon-to-carbon unsaturation.

6. A method of claim 4 wherein said source batch material for tin is a stannous salt of a $C_1$ to $C_4$ acyclic monocarboxylic acid containing no ethylenic or acetylenic carbon-to-carbon unsaturation.

* * * * *